United States Patent [19]

Boland et al.

[11] Patent Number: 5,467,495

[45] Date of Patent: Nov. 21, 1995

[54] BRUSH FOR AN ELECTRICALLY POWERED TOOTHBRUSH

[75] Inventors: Bernhard Boland, Frankfurt/M.; Peter Hilfinger, Bad Homburg, both of Germany

[73] Assignee: Braun Aktiengesellschaft, Germany

[21] Appl. No.: 320,558

[22] Filed: Oct. 11, 1994

Related U.S. Application Data

[63] Continuation of Ser. No. 8,619, Jan. 22, 1993, abandoned.

[30] Foreign Application Priority Data

Jan. 24, 1992 [DE] Germany .......................... 42 01 873.0

[51] Int. Cl.⁶ ............................ A46B 9/04; A46B 13/02
[52] U.S. Cl. ...................... 15/28; 15/DIG. 5; 15/207.2; 15/180
[58] Field of Search ..................... 15/28, 29, 207.2, 15/DIG. 5, DIG. 6, 49.1, 26, 180

[56] References Cited

U.S. PATENT DOCUMENTS

| | | | |
|---|---|---|---|
| 430,077 | 6/1890 | Jenness | 15/DIG. 6 |
| 1,206,031 | 11/1916 | Ritter et al. | 15/DIG. 6 |
| 1,267,282 | 5/1918 | Scully | 15/28 |
| 1,320,616 | 11/1919 | Hampe | 15/28 |
| 1,372,988 | 3/1921 | Wilson | 15/29 |
| 1,391,882 | 9/1921 | Dworniczak | 15/28 |
| 1,604,500 | 10/1926 | Tannenbaum | 15/29 |
| 1,890,943 | 12/1932 | Hoffman | 15/28 |
| 1,896,731 | 2/1933 | Lippett | 15/28 |
| 2,100,138 | 11/1937 | Heldt | 15/DIG. 6 |
| 2,140,307 | 12/1938 | Belaschk et al. | 15/28 |
| 2,186,520 | 1/1940 | Burkinshaw | 15/28 |
| 3,047,898 | 8/1962 | Levite | 15/DIG. 6 |
| 3,072,944 | 1/1963 | Clayton et al. | 15/DIG. 6 |
| 3,115,652 | 12/1963 | Zerbee | 15/28 |
| 3,802,420 | 4/1974 | Moffat et al. | 15/28 |
| 4,037,369 | 7/1977 | Campbell | 15/180 |
| 4,074,385 | 2/1978 | Howard et al. | 15/180 |
| 4,114,225 | 9/1978 | Malish et al. | 15/DIG. 5 |
| 4,619,009 | 10/1986 | Rosenstatter | 15/29 |
| 4,679,270 | 7/1987 | Gaiti et al. | 15/29 |
| 4,686,729 | 8/1987 | Roman et al. | 15/29 |
| 4,686,918 | 8/1987 | Hjalmer et al. | 15/180 |
| 5,142,724 | 9/1992 | Park | 15/28 |

FOREIGN PATENT DOCUMENTS

| | | | |
|---|---|---|---|
| 40406 | 9/1968 | Finland | 15/29 |
| 1063397 | 12/1953 | France | 15/28 |
| 1337633 | 8/1963 | France | 15/180 |
| 325149 | 9/1920 | Germany . | |
| 1935020 | 3/1965 | Germany . | |
| 88 07 968.6 | 6/1988 | Germany . | |
| 3833496 | 8/1989 | Germany | 15/29 |
| 21648 | 2/1978 | Japan | 15/180 |
| 39918 | 6/1907 | Switzerland | 15/DIG. 5 |
| 409857 | 10/1966 | Switzerland | 15/180 |
| 191507 | 10/1921 | United Kingdom | 15/29 |
| 452961 | 9/1936 | United Kingdom | 15/28 |
| 1447943 | 9/1976 | United Kingdom . | |
| 2220845 | 1/1990 | United Kingdom | 15/28 |
| 8900388 | 1/1989 | WIPO | 15/28 |
| WO91/07116 | 5/1991 | WIPO . | |

*Primary Examiner*—David Scherbel
*Assistant Examiner*—Tony G. Soohoo
*Attorney, Agent, or Firm*—Fish & Richardson

[57] ABSTRACT

The invention is directed to a brush for an electric toothbrush, comprising a cylindrical bristle supporting structure equipped with bristles arranged on several approximately concentric circular rings on the bristle supporting structure. A circular ring devoid of bristles is maintained between at least two adjacent bristled circular rings, with the average width of the bare circular ring corresponding approximately to the average width of a bristled circular ring. The brush is adapted to perform an oscillating movement vertically to the longitudinal axis of the toothbrush. As a special brush, it is particularly well suited to the cleaning of teeth of persons wearing orthodontic appliances.

8 Claims, 3 Drawing Sheets

BRUSH FOR AN ELECTRICALLY POWERED TOOTHBRUSH

This is a continuation of application Ser. No. 08/008,619, filed Jan. 22, 1993, now abandoned.

This invention relates to a brush for an electrically powered toothbrush, comprising a cylindrical bristle supporting structure equipped with bristles. These bristles are arranged on the bristle supporting structure in several approximately concentric circular rings. The bristle supporting structure is adapted to perform oscillating movements vertically to the longitudinal axis of the toothbrush by means of the electric driving unit.

A brush of this type is known from International Patent Application No. WO 91/07116 filed by the applicant. In this brush, the bristle supporting structure has its entire surface set with bristles. In combination with the oscillating driving unit, the brush has proven to be successful in practical use, enabling the average user to obtain very good cleaning results within a relatively short cleaning period only. However, if the brush is used for cleaning the teeth of users wearing orthodontic appliances, the problem exists that the bristles arranged in the center area bear against the brackets of the orthodontic appliance. Therefore, the outer bristles have difficulties reaching the tooth surface behind the bracket, as a result of which the cleaning effect of the known brushes may be reduced in this special application.

From printed specification DE-PS 325149 a hand-operated twin brush for cleaning teeth is known in which each brush is comprised of two round brushes. These may be penicilliform or mushroom-shaped, but are of identical height. In the cleaning of teeth provided with orthodontic appliances, this relative arrangement of the brushes involves equally the drawback of the brushes bearing against the brackets, again making it hard to reach the teeth behind the brackets.

In addition, printed specification DE 88 07 968 U1 discloses a brush head for an electric toothbrush which is comprised of two sets of concentrically arranged tufts of bristles surmounted by a central tuft. This central tuft of bristles includes a conically tapering end section and has a larger maximum diameter and a higher stiffness than the concentric tufts. In the practical use of this brush head, the central tuft bears against the brackets or the tooth surface, so that a cleaning action by the remaining concentrically arranged tufts of bristles is produced to an insufficient degree only or not at all.

It is an object of the present invention to devise a brush for an electrically powered toothbrush which produces good cleaning results when used as a special brush by wearers of orthodontic appliances and eliminates the risk of damage of the orthodontic appliances.

This object is essentially accomplished by a brush incorporating the features initially referred to, in which a circular ring devoid of bristles is maintained between at least two adjacent circular rings on which bristles are provided. In this arrangement, the average width of the bare circular ring is approximately equal to the average width of a bristled circular ring. When the brush is used for cleaning the teeth of persons wearing orthodontic appliances, the absence of bristles on the one circular ring reduces or nearly avoids the undesired bearing action of the bristles against the brackets. Because the width of the bare circular ring is approximately the same as the width of the bristled circular rings, the bristles of the inner circular ring or rings may readily escape outwardly as soon as an obstacle as a bracket of the orthodontic appliance blocks their way. It is thereby ensured that the bristles on the outer circular ring are maintained in contact with the tooth surface, in particular in the area behind the brackets— when brushing is performed at an angle—, creating a good cleaning action of this surface due to the oscillating driving unit.

In an embodiment of the present invention, the selected lengths of the bristles on the different circular rings vary. In the present application, this enables the length of the bristles to be individually adapted to the surface to be cleaned. This has an advantageous effect on the cleaning action, in particular in combination with the wiping motion caused by oscillation of the brush and removing dental plaque more effectively.

By providing the bristles on the outer circular ring with a length of between 6 and 10 mm, approximately, in particular 8 +/–0.5 mm, and the bristles on the inner circular ring with a length of between 4 and 9 mm, approximately, in particular 7.2 +/–0.5 mm, an advantageous dimensioning of the bristle length is obtained in which the outer bristles are capable of reaching the teeth behind the brackets as well as the gum line, while the shorter bristles engage against the brackets, yet without damaging them.

In view of the special application of the brush, in an advantageous embodiment of the present invention varying degrees of thickness are selected for the bristles on the individual circular rings in order to be able to remove dental plaque more effectively, particularly in the corners of the brackets, and create an optimum cleaning action.

The greater thickness of 7 +/–2 mils (1 mil corresponding to 0.0254 mm) and consequently greater hardness was selected for the outer bristles, because these bristles are intended to clean the tooth behind the wire or the area where the brackets are cemented, while the inner bristle ring, with a bristle thickness of 5 +/–2 mils, is especially suitable for cleaning the brackets, accomplishing a good cleaning result without damaging the brackets.

The provision of three tufts of bristles of like density, yet reduced thickness, on the inner circular ring proves advantageous because each individual tuft bears against the brackets resiliently during the cleaning operation, cleaning them with the aid of the oscillating movement and without applying too great a pressure, thereby counteracting potential damage.

In an advantageous embodiment of the present invention, the three tufts of bristles on the inner circular ring are disposed at a relative angle of 120°, thus resulting in a uniform distribution of the pressure acting on the brackets during the cleaning operation.

Further features, advantages and application possibilities of the present invention will become apparent from the subsequent description of an embodiment illustrated in more detail in the accompanying drawings. It will be understood that all features described and/or represented by illustration, whether taken alone or in any desired combination, constitute the subject-matter of the present invention, irrespective of their summarization in the claims and their back-references. In the drawings, FIG. 1 is a schematic side view of an electric toothbrush;

FIG. 2b is a longitudinal sectional view of the brush taken along the line A—A of FIG. 2a.

Figure 1:
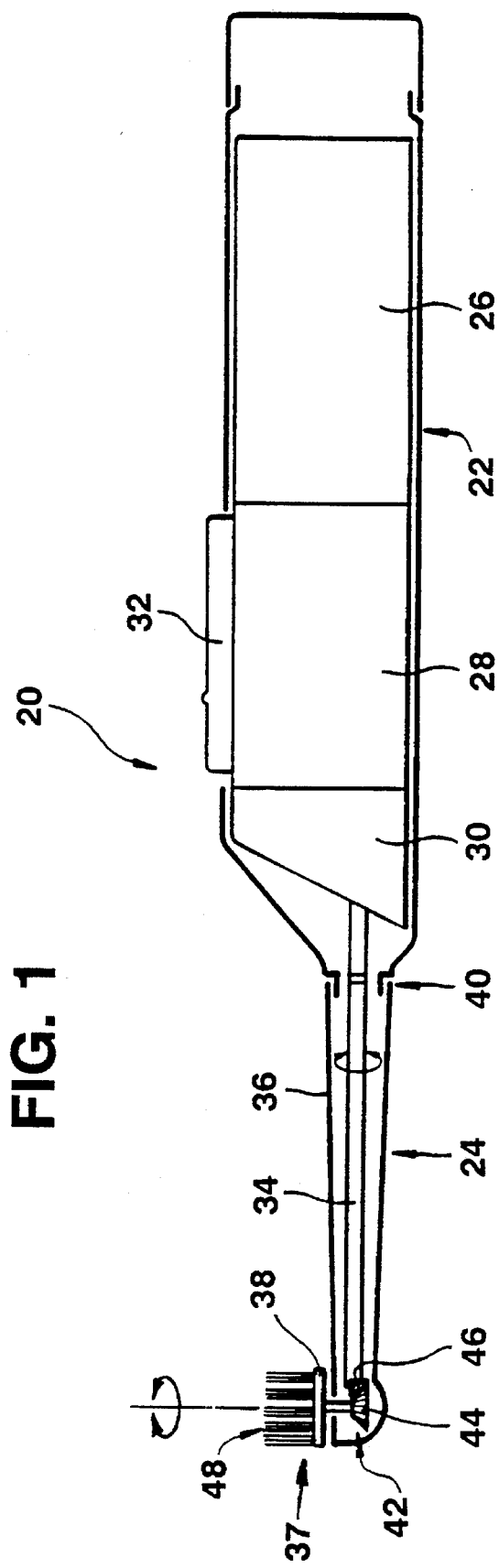

Referring now to FIG. 1 of the drawings, reference numeral 20 identifies an electric toothbrush. The toothbrush 20 comprises a handle section 22 and a brush section 24 adapted to be coupled thereto. The handle section 22 accommodates an accumulator 26 or, alternatively, a battery, an electric motor 28 as well as a driving mechanism 30 for transforming the continuous rotary motion of the electric motor into an oscillatory motion. A switch 32 for activation of the toothbrush 20 is provided on the outside of the handle section 22. The brush section 24 includes a hollow mounting tube 36 receiving a shaft 34. The mounting tube 36 and the shaft 34 are adapted to be connected with the handle section 22 by a coupling means 40 not shown in greater detail. At the end of the brush section 24 remote from the handle section 22, a bristle supporting structure 38 is provided for receiving bristles 48 or tufts of bristles. Through a bevel gear 44 at the end of the bristle supporting structure 38 and a mating bevel gear segment 46 at the head end of the shaft 34, the brush 37 is caused to perform an oscillating movement. The range of the angle of rotation covered by the bristle supporting structure 38 preferably assumes a value in the range of +/−35° +/−5°, approximately, with values in the range of between +/−20° and +/−100° being, however, also possible. The axis of rotation of the bristle supporting structure 38 defines an angle of 90°, approximately, with respect to the axis of rotation of the shaft 34. The toothbrush of FIG. 1 is described in detail in pending U.S. patent application Ser. No. 07/855,640, filed May 4, 1992, now abandoned.

Figure 2B:
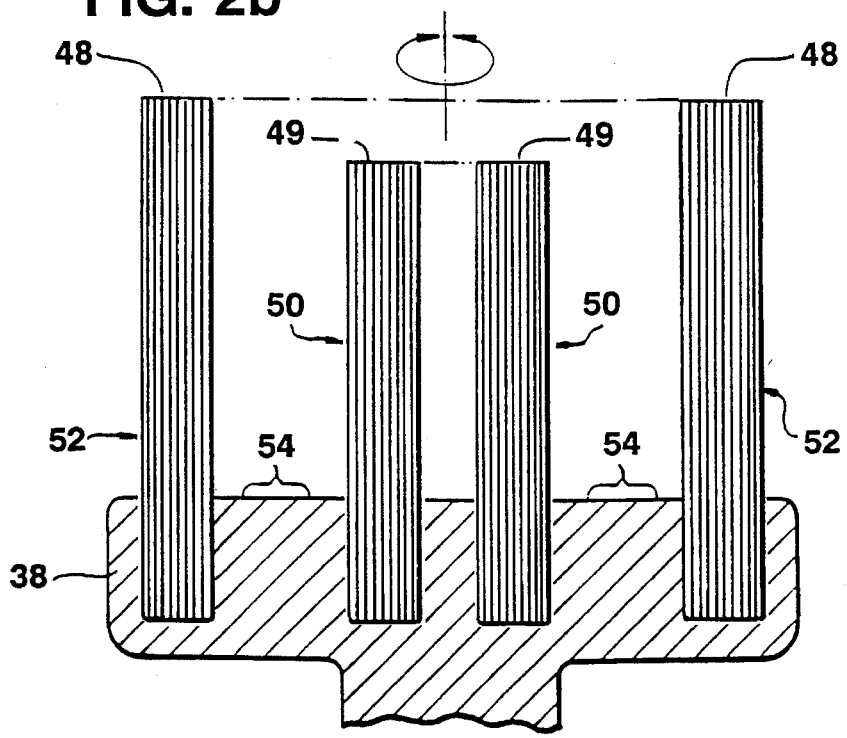
Figure 2A:
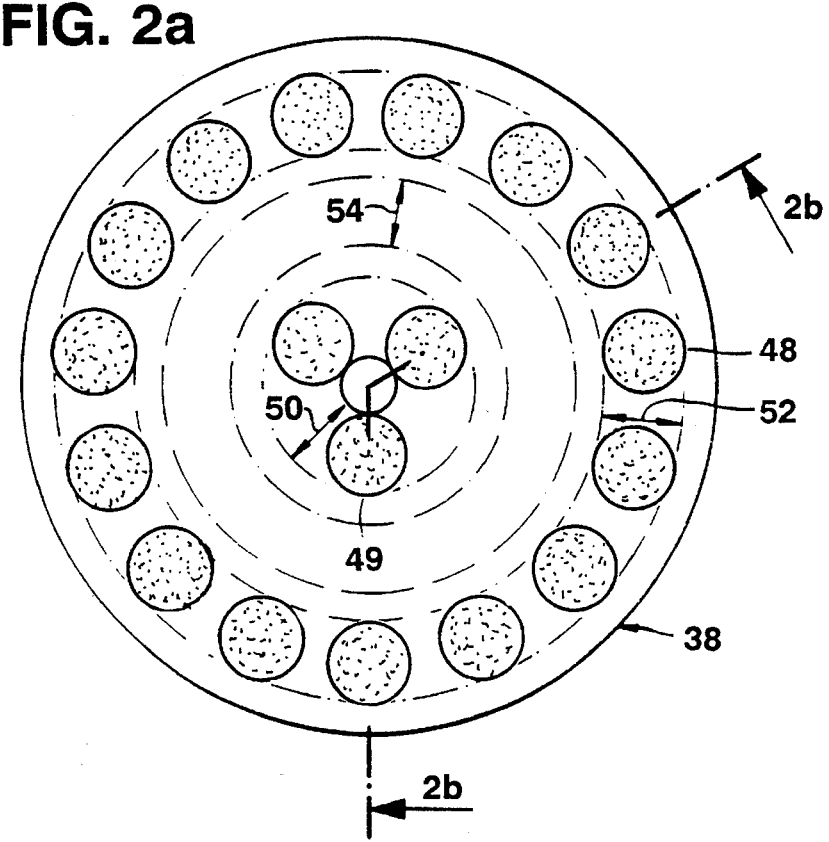
FIG. 2a is a top plan view of the bristle supporting structure including the bristles.

FIG. 2a shows the arrangement of the bristles 48 and 49 on the bristle supporting structure 38. The arrangement is such as to provide two approximately concentric circular rings 50, 52, whereof the outer circular ring 52 is set with bristles 48 distributed uniformly over the entire circular ring, while the bristles 49 on the inner circular ring 50 are arranged at relative angles of 120°. A circular ring 54 on which no bristles are provided is situated intermediate the two circular rings 50, 52.

The length of the bristles 48 and 49 and the arrangement of the relative distances of the circular rings 50, 52 and 54 on the bristle supporting structure 38 will appear from the representation of FIG. 2b. While the outer circular ring 52 is equipped with longer bristles 48, the inner circular ring 50 is set with shorter bristles 49. The bare circular ring 54 lies between the two circular rings 50, 52.

Figure 2C:
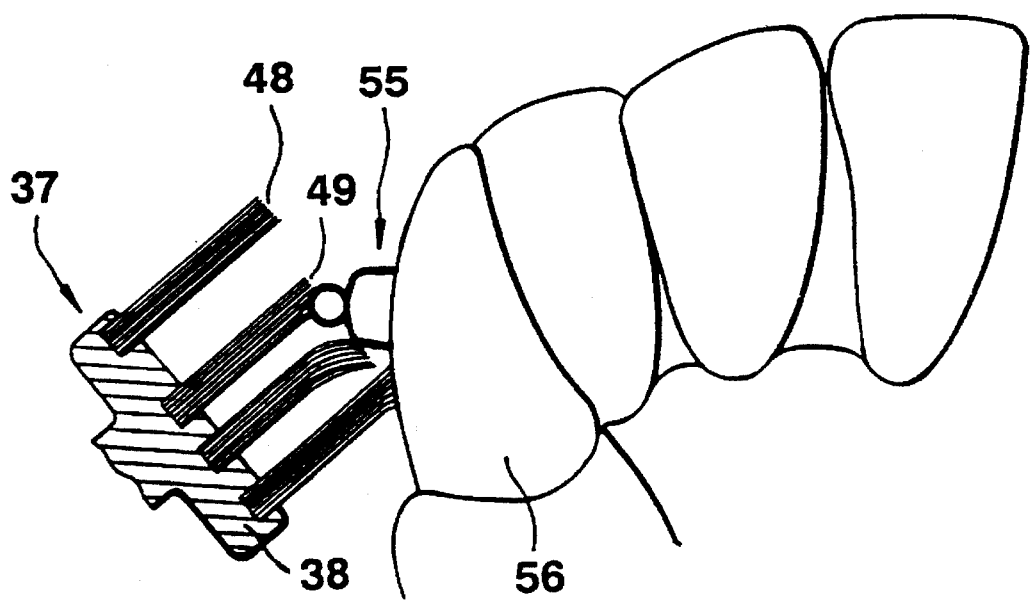
FIG. 2c is a view of the brush illustrating it in a special position to explain the cleaning action.

FIG. 2c illustrates one of several advantageous positions of the brush 37 when cleaning teeth to which orthodontic appliances with brackets 55 are fitted. The section through the brush 37 shows clearly the different uses of the bristles 48 and 49 with respect to the brackets 55. A slight tilt of the brush 37, in combination with the oscillating movement which causes bending of the bristles in an extremely advantageous manner in a direction opposite to the direction of rotation of the brush and, on reversal of the direction of rotation, a brief raising of the bristles, additionally intensifies the cleaning effect, in particular in the area where the brackets are cemented.

We claim:

1. A brush attachment structure for an electric toothbrush having a handle section, said brush attachment structure comprising an elongated hollow mounting tube with a coupling end for coupling to the handle section, a cylindrical bristle supporting structure mounted at an end of said mounting tube opposite said coupling end and having an axis of rotation that is oriented in a transverse direction relative to a longitudinal axis of said mounting tube, a shaft and gear mechanism within said mounting tube for transmitting a drive motion from the handle section to the bristle supporting structure, said drive motion causing said supporting structure to perform oscillating movements about its axis of rotation, said bristle supporting structure having bristles arranged thereon so as to be fully contained within approximately concentric bristle containing annular cylindrical regions, each region having a wall thickness and wherein at least two adjacent concentric bristle containing regions are separated by an annular cylindrical region devoid of bristles and having a wall thickness that is larger than the wall thickness of at least one of the concentric bristle containing regions on either side thereof.

2. The brush as claimed in claim 1, wherein the lengths of the bristles in the bristle containing cylindrical region on one side of said annular cylindrical region devoid of bristles are different from the lengths of the bristles in the bristle containing cylindrical region that is one the other side of said annular cylindrical region devoid of bristles.

3. The brush as claimed in claim 1 or claim 2, wherein the two adjacent bristle containing cylindrical regions that are separated by the annular cylindrical region devoid of bristles include an outer cylindrical region and an inner cylindrical region and wherein the length of the bristles arranged in the outer cylindrical region is in the range of between 6 and 10 mm and the length of the bristles arranged in the inner cylindrical region is in the range of between 4 and 9 mm.

4. The brush as claimed in claim 1 or claim 2, wherein the two adjacent bristle containing cylindrical regions that are separated by the annular cylindrical region devoid of bristles include an outer cylindrical region and an inner cylindrical region and wherein the thickness of the bristles in the outer cylindrical region is different from the thickness of the bristles in the inner cylindrical region.

5. The brush as claimed in claim 4, wherein the thickness of the bristles arranged in the outer cylindrical region is 7 +/−2 mils, and the thickness of the bristles arranged in the inner cylindrical region is 5 +/−2 mils.

6. The brush as claimed in claim 1 or claim 2, bristle containing cylindrical regions that are separated by the annular cylindrical region devoid of bristles include an outer cylindrical region and an inner cylindrical region and wherein the bristles in the inner cylindrical region are grouped to form three tufts of bristles of like density.

7. The brush as claimed in claim 6, wherein the three tufts of bristles arranged in the inner cylindrical region are disposed at a relative angle of 120°.

8. A brush attachment structure for an electric toothbrush having a handle section, said brush attachment structure comprising an elongated hollow mounting tube with a coupling end for coupling to the handle section, a cylindrical bristle supporting structure mounted at an end of said mounting tube opposite said coupling end and having an axis of rotation that is oriented in a transverse direction relative to a longitudinal axis of said mounting tube, a shaft and gear mechanism within said mounting tube for transmitting a drive motion from the handle section to the bristle supporting structure, said drive motion causing said supporting structure to perform oscillating movements about its axis of rotation, said bristle supporting structure having bristles arranged thereon, each of said bristles having a first end attached to said bristle supporting structure and a second free end, wherein said free ends are arranged in approximately concentric bristle containing circular rings, each concentric bristle containing circular ring having a width, wherein said free ends on one concentric bristle containing circular ring are spaced from said free ends on at least one adjacent concentric bristle containing circular ring by a circular ring devoid of bristles and having a width that is larger than the width of at least one of the concentric circular rings.

* * * * *